United States Patent [19]
Wright

[11] Patent Number: 5,340,129
[45] Date of Patent: Aug. 23, 1994

[54] SAW BLADE RETENTION SYSTEM

[75] Inventor: David W. Wright, Novi, Mich.

[73] Assignee: Minnesota Mining and Manufacturing Company, St. Paul, Minn.

[21] Appl. No.: 6,814

[22] Filed: Jan. 21, 1993

[51] Int. Cl.$^5$ .......................... B26D 1/08; B27B 19/09
[52] U.S. Cl. ....................................... 279/90; 30/337; 30/392; 30/351; 83/697; 606/82; 606/177
[58] Field of Search ................................ 279/89–91; 30/337–339, 392–394, 351; 83/697, 698; 606/82, 177

[56] References Cited

U.S. PATENT DOCUMENTS

| | | | |
|---|---|---|---|
| 2,282,902 | 5/1942 | Sultan | 30/519 |
| 2,408,567 | 10/1946 | Mauch | 279/93 |
| 2,703,716 | 3/1955 | Shore | 279/93 |
| 3,927,893 | 12/1975 | Dillon et al. | 279/75 |
| 3,943,934 | 3/1976 | Bent | 128/317 |
| 4,020,555 | 5/1977 | Hedrick | 30/392 |
| 4,386,609 | 6/1983 | Mongeon | 128/317 |
| 4,528,753 | 7/1985 | Kuhlmann et al. | 30/392 |
| 4,626,146 | 12/1986 | Neumaier | 408/239 |
| 4,691,929 | 9/1987 | Neumaier et al. | 179/19.3 |
| 4,872,452 | 10/1989 | Alexson | 128/92 |

FOREIGN PATENT DOCUMENTS 4102011  12/1991  Fed. Rep. of Germany ........ 279/90

OTHER PUBLICATIONS

Brochure entitled "Sarns-Sternal Saw System-Operators Manual" Sarns 3M Health Care, dated Dec., 1989.
Brochure entitled "Sarns Auxiliary Cardiovascular Equipment" of Sarns 3M Health Care, dated 1989.
Poster entitled "Cleaning the Sarns Sternal Saw/Limpieza de la Sierra Sarns Sternal" of Sarns, Form No. 16087100.

*Primary Examiner*—Steven C. Bishop
*Attorney, Agent, or Firm*—Gary L. Griswold; Walter N. Kirn; Stephen W. Bauer

[57] ABSTRACT

A saw blade retention system for retaining a saw blade to a reciprocating saw includes a shaft connected to the saw for reciprocation and having a slot for receiving the saw blade. The saw blade retention system also includes a chuck disposed about the shaft and having a slot aligned with the slot in the shaft in an unlocked position for allowing the saw blade to be disposed in the slot for the shaft. The saw blade retention system further includes a cam-type mechanism for allowing the chuck to rotate angularly relative to the saw blade and shaft to a locked position to prevent the saw blade from exiting the slots and for allowing the chuck to move axially relative to the shaft to prevent axial movement of the saw blade between the chuck and the shaft. Complementary inclined surfaces are provided on the blade and the chuck to center the blade relative to its intended path of reciprocation.

22 Claims, 3 Drawing Sheets

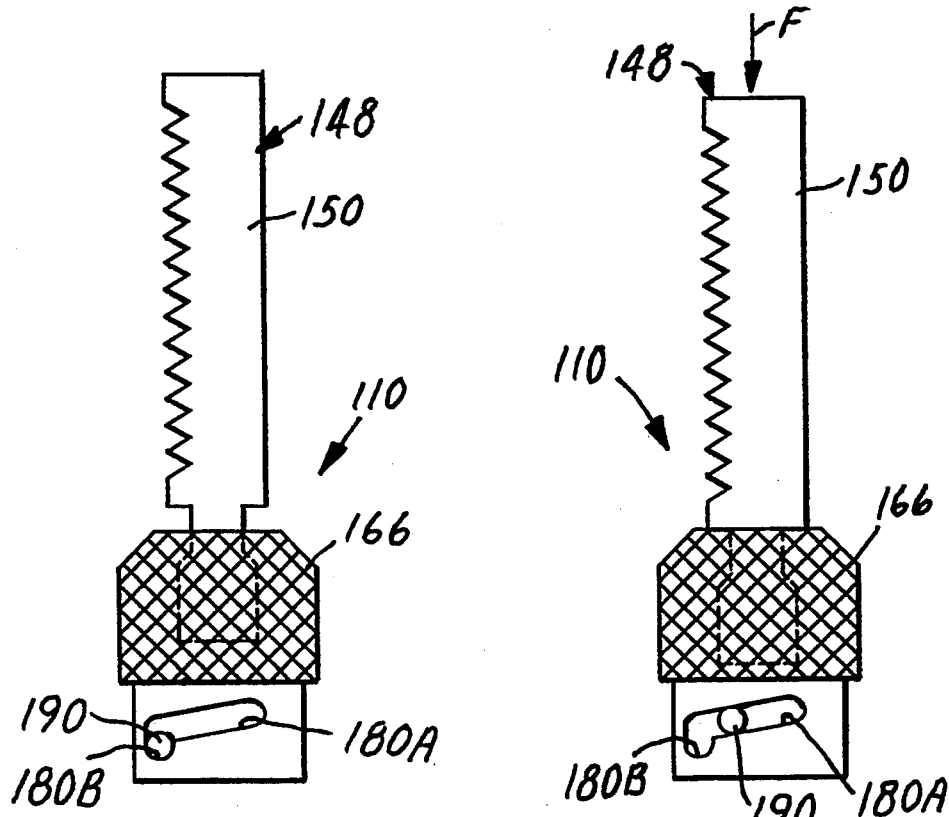
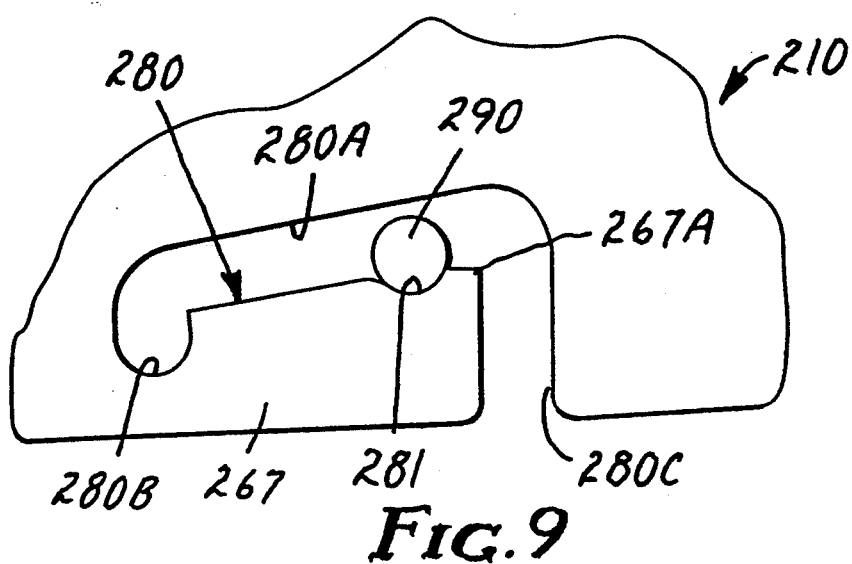

SAW BLADE RETENTION SYSTEM

BACKGROUND OF THE INVENTION

1. Field of the Invention

The present invention relates generally to saws and, more particularly, to a saw blade retention system for a reciprocating surgical saw.

2. Description of the Related Art

Generally, a reciprocating saw known as a "sternal saw" is used in splitting a sternum of a patient during thoracic surgery by cutting from either the suprasternal notch or the xiphoid process. Typically, the sternal saw is driven through a flexible drive shaft by an electric motor which may be operated by a foot control. The sternal saw includes a reciprocating shaft and saw blade. The saw blade is removably secured to the reciprocating shaft by a fastener such as a screw.

One disadvantage of the above sternal saw is that the saw blade may rotate about the screw relative to the reciprocating shaft. Another disadvantage is that it is not convenient to change the saw blade after sterilization of the sternal saw. Yet another disadvantage is that a tool such as a screwdriver is required to change the saw blade. Still another disadvantage is that the saw blade and screw are packaged together which is undesired. A further disadvantage is that the screw increases the cost for changing or replacing the saw blade.

One sternal saw that has been in wide use has been sold by Minnesota Mining and Manufacturing Company, St. Paul, Minn., under the trade designation "SARNS" Sternal Saw, Catalog No. 6090.

SUMMARY OF THE INVENTION

Accordingly, the present invention is a saw blade retention system for retaining a saw blade to a reciprocating saw. The saw blade retention system includes a shaft connected to the saw for reciprocation and having receiving means for receiving a saw blade. The saw blade retention system also includes a chuck disposed about the shaft and having alignment means aligned with the receiving means in an unlocked position for allowing the saw blade to be disposed in the receiving means. The saw blade retention system further includes rotation means for allowing the chuck to rotate angularly relative to the saw blade and shaft to a locked position to prevent the saw blade from exiting the receiving means and for allowing the chuck to move axially relative to the shaft to prevent axial movement of the saw blade between the chuck and shaft.

Moreover, the present invention is a saw blade for retention to a reciprocating saw. The saw blade includes a blade portion having a plurality of teeth and a shank portion extending from the blade portion for connection to a reciprocating saw. The saw blade also includes means forming a pair of recesses opposing each other from edges of the shank portion. The shank portion has a planar end edge, planar side edges generally perpendicular to the end edge and planar inclined edges extending from the side edges into the recesses and away from the end edge.

One advantage of the present invention is that a saw blade retention system is provided for removably retaining a saw blade to a reciprocating or sternal saw. Another advantage of the present invention is that the saw blade retention system incorporates a self-centering blade feature which provides axial and radial locking action by a three point pinch, trapping the saw blade to prevent movement thereof. Yet another advantage of the present invention is that the saw blade retention system eliminates the use of screws and screwdrivers. A further advantage of the present invention is that the saw blade retention system allows for added convenience and decreases the cost of changing or replacing the saw blade.

Other objects, features and advantages of the present invention will be readily appreciated as the same becomes better understood after reading the following description taken in conjunction with the accompanying drawings.

BRIEF DESCRIPTION OF THE DRAWINGS

The invention will be further described with reference to the drawing wherein corresponding reference numerals indicate corresponding parts throughout the several views of the drawing, and wherein:

FIG. 7 is an elevational view, similar to FIG. 4, of another embodiment of the saw blade retention system, showing a blade-retaining chuck held in its blade-releasing position;

FIG. 8 is an elevational view similar to FIG. 7 showing the blade-receiving chuck in its blade-securing position; and FIG. 9 is a view of a portion of the blade-receiving chuck illustrating yet another embodiment of the saw blade retention system of the invention.

DESCRIPTION OF THE PREFERRED EMBODIMENT(S)

Figure 1:
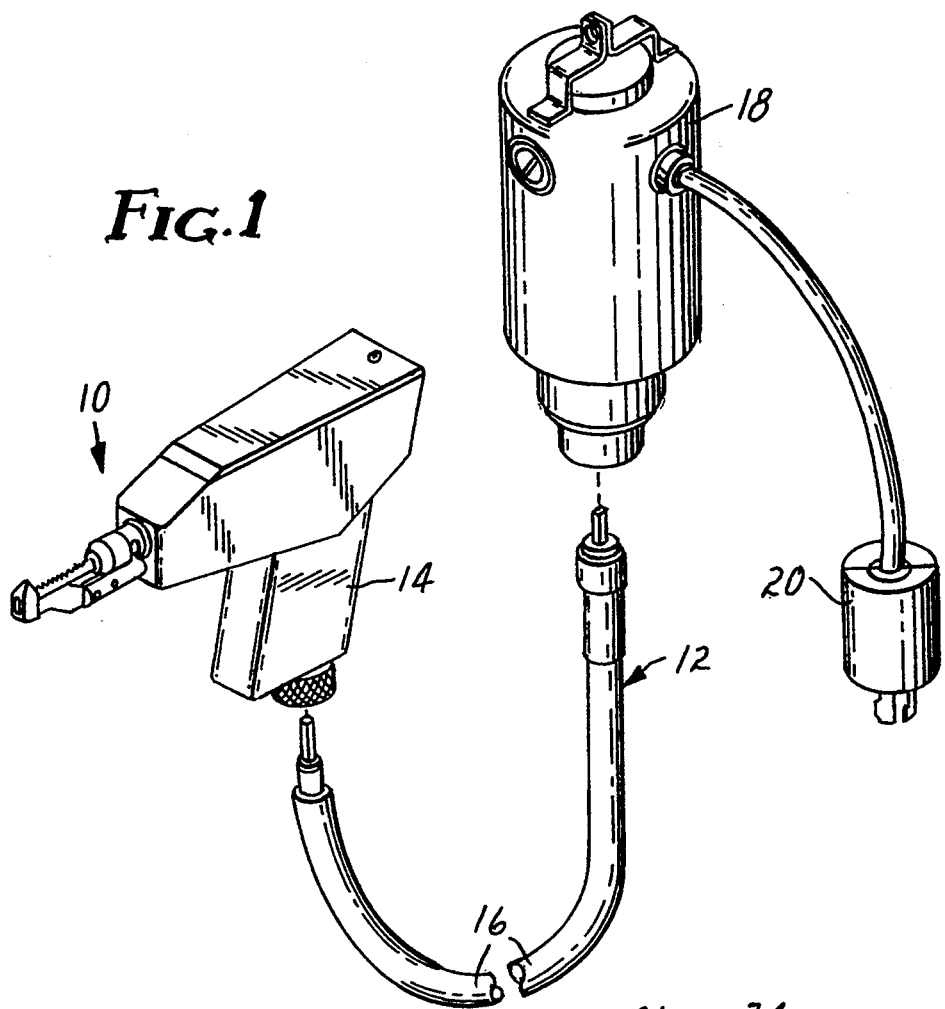
FIG. 1 is a perspective view of a saw blade retention system, according to the present invention, illustrated in operational relationship to a sternal saw system.

Referring to the drawings and in particular to FIG. 1 thereof, a saw blade retention system 10, according to the present invention, is illustrated in operational relationship to a reciprocating or sternal saw system, generally indicated at 12. The sternal saw system 12 includes a sternal saw 14 driven through a flexible drive shaft 16 by an electric motor 18. The electric motor 18 has a plug 20 for connection to a foot control (not shown) which, in turn, is connected to a source of electrical power (not shown).

Figure 2:
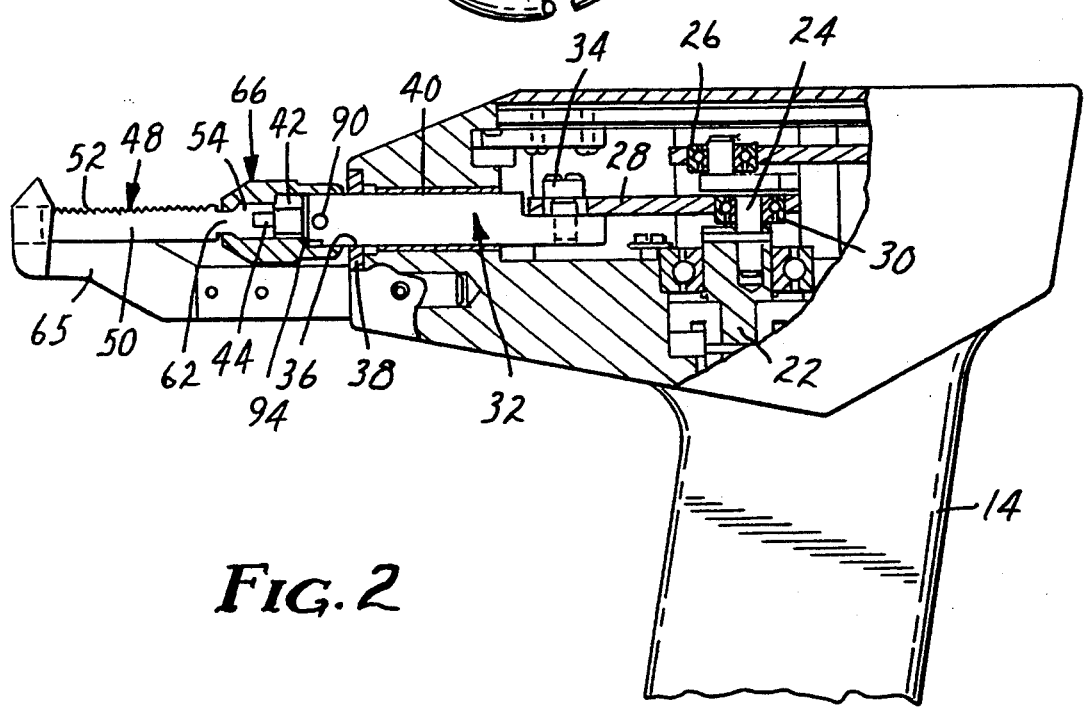
FIG. 2 is a fragmentary elevational view of the saw blade retention system and a sternal saw of the sternal saw system of FIG. 1.

Referring to FIG. 2, the sternal saw 14 is a reciprocating saw designed for use in splitting a sternum of a patient during thoracic surgery. The sternal saw 14 has a conventional rotatable shaft 22 which is operatively rotated by the drive shaft 16. The sternal saw 14 also has a conventional eccentric member 24 having a first shaft mounted in a bearing 26 in the housing of the sternal saw 14 for rotation along a common axis of rotation with the rotatable shaft 22, and an eccentric shaft connected to the rotatable shaft 22 and offset from the axis of rotation of the rotatable shaft 22. The sternal saw 14 further has a reciprocating shaft 28 mounted on the eccentric shaft of the eccentric member 24 by a bearing 30. The arrangement is such that rotation of shaft 22 rotates the eccentric member 24, in turn, reciprocating the shaft 28 along its axis of reciprocation. A sternal saw having rotatable, eccentric and reciprocating shafts for reciprocating a blade has been available from Minnesota Mining and Manufacturing Company, St. Paul, Minn., under the trade designation "SARNS" Sternal Saw, Catalog No. 6090.

Figure 3:
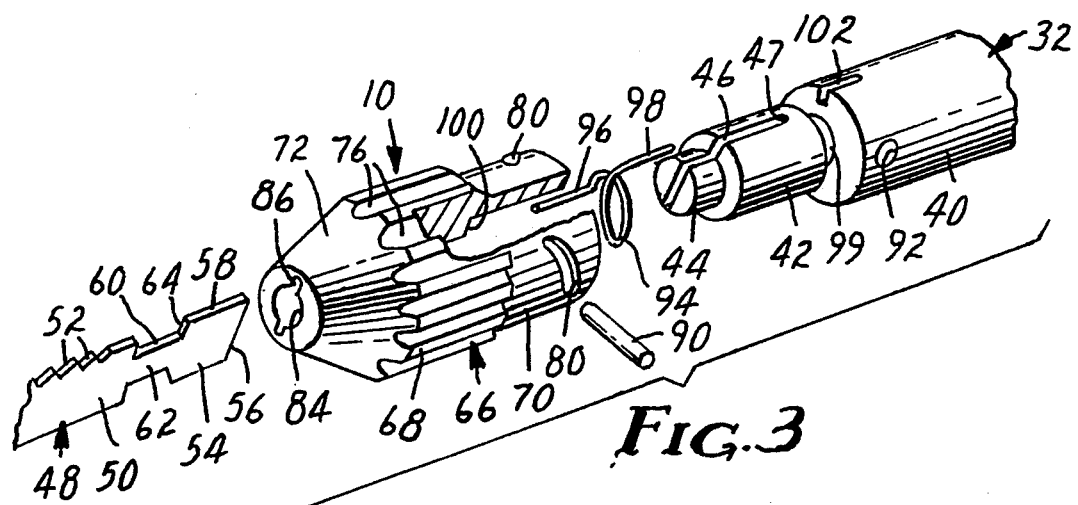
FIG. 3 is an exploded perspective view of the saw blade retention system of FIGS. 1 and 2.
Figure 4:
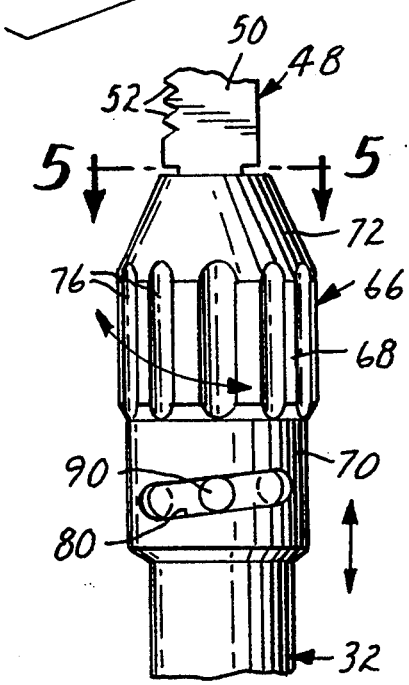
FIG. 4 is an elevational view of the saw blade retention system of FIGS. 1 through 3.

Referring to FIGS. 2 and 3, the novel saw blade retention system 10, according to the present invention, includes a retention shaft, generally indicated at 32. The retention shaft 32 is connected to the reciprocating shaft 28 by suitable means such as a fastener 34. Alternatively, the retention shaft 32 and the reciprocating shaft 28 could be one, integral piece. The retention shaft 32 is generally cylindrical in shape and extends longitudinally through an aperture 36 in a bushing 38 at one end of the sternal saw 14. It should be appreciated that the retention shaft 32 reciprocates due to the movement of the reciprocating shaft 28 of the sternal saw 14.

The retention shaft 32 has a main portion 40 and a first stepped portion 42 at one end of the main portion 40. The first stepped portion 42 has a diameter less than a diameter of the main portion 40. The retention shaft 32 also includes a second stepped portion 44 at the end of the first stepped portion 42 and having a diameter less than a diameter of the first stepped portion 42. The retention shaft 32 further includes a blade-receiving aperture or slot 46 extending axially through the second stepped portion 44 and into the first stepped portion 42 to a blade seat 47 for a function to be described.

The saw blade retention system 10 also includes a generally flat, elongate saw blade, generally indicated at 48. The saw blade 48 has a generally elongate blade portion 50 extending axially/longitudinally with a plurality of teeth 52. The saw blade 48 also has a shank portion 54 extending axially/longitudinally from the blade portion 50. In use, the shank portion 54 is disposed in the blade-receiving slot 46 of the retention shaft 32. The shank portion 54 is generally pentagonal in shape and has an end edge 56 which is linear or planar and side edges 58 which are linear or planar and generally perpendicular to the end edge 56.

Figure 6:
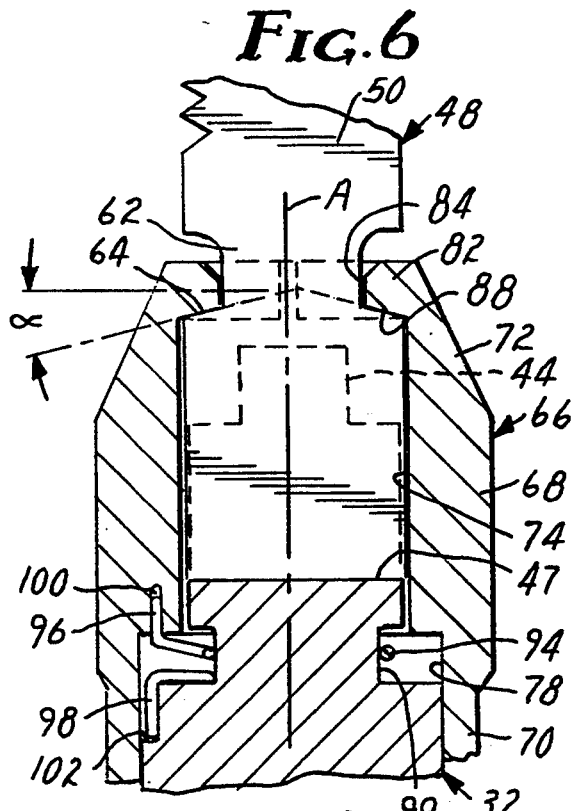
FIG. 6 is a fragmentary view of the saw blade retention system of FIG. 4 illustrating the saw blade retention system in a locked position.

The shank portion 54 also has recesses 60 axially/longitudinally aligned and extending toward each other from opposite edges of the shank portion 54 to form a reduced portion 62 having a width less than a width of the shank portion 54. The shank portion 54 also has inclined edges 64 extending from the side edges 58 to the reduced portion 62 and toward the blade portion 50. The inclined edges 64 preferably extend at an angle ("α" in FIG. 6) of approximately 20 degrees relative to the lateral direction (i.e., the direction along the major surfaces of the blade 48 perpendicular to the longitudinal direction of the blade 48). As illustrated in FIGS. 1 and 2, the blade portion 50 may be supported at its free end by a conventional foot piece 65 connected to the sternal saw 14.

Referring to FIGS. 2 through 4 and 6, the saw blade retention system 10 further includes a chuck, generally indicated at 66, for removably retaining or securing the saw blade 48 to the retention shaft 32. The chuck 66 is generally tubular and has a body portion 68 and a stem portion 70 at one axial end and a seating portion 72 at the other axial end. The body portion 68 is generally cylindrical in shape and has a first pocket 74 of a diameter to receive the shank portion 54 of the saw blade 48. The body portion 68 also has an outer surface formed with a plurality of recesses 76 extending axially and spaced laterally to form a gripping surface for a hand of an operator. It should be appreciated that the outer surface of the body portion 68 may be formed as a gripping surface by any suitable means such as knurling.

The stem portion 70 extends axially from the body portion 68 and is generally cylindrical in shape. The stem portion 70 has an outer surface of a diameter less than a diameter of the outer surface of the body portion 68. The stem portion 70 also has a second pocket 78 of a diameter to receive the main portion 40 of the retention shaft 32. The second pocket 78 has a diameter greater than a diameter of the first pocket 74. The stem portion 70 further has at least one, preferably a pair of, cam grooves or slots 80 opposing each other and extending circumferentially and axially (e.g., helically) a predetermined amount. For example, the cam slots 80 extend circumferentially about sixty-nine degrees (69°), axially forty-five thousandths (0.045) of an inch (1.14 mm), and have a helix angle of approximately 8 degrees relative to the axis of rotation of the chuck 66. It should be appreciated that the cam slots 80 may have any suitable circumferential or axial length for a function to be described.

The seating portion 72 is generally frustoconical in shape and extends axially from the body portion 68. The seating portion 72 has an annular ledge 82 at the end thereof which extends radially inwardly to form an aperture 84 having a diameter less than the diameter of the first pocket 74. The ledge 82 has a blade aperture or slot 86 extending axially through the ledge 82 of a width sufficient to allow the shank portion 54 to be received or disposed within the first pocket 74. It should be appreciated that the aperture 84 is of a sufficient diameter to allow the second stepped portion 44 of the retention shaft 32 to be received or disposed therein.

The seating portion 72 also has an interior surface 88 on ledge 82 which is conical or inclined toward the aperture 84 at a predetermined angle, such as twenty degrees (20°), for example, approximately equal to and complementary with the angle of the inclined edges 64 of the blade 48. The interior surface 88 mates or cooperates with the inclined surfaces 64 of the shank portion 54 to center the saw blade 48 relative to an axial axis A of the retention shaft 32. It should be appreciated that the inclined surface 88 of the chuck 66 moves the shank portion 54 radially due to the contact between the inclined surface 88 and inclined edges 64 to center the saw blade 48. It should also be appreciated that the interior surface 88 cooperates with the shank portion 54 to provide a positive radial locking force to prevent radial movement of the saw blade 48 relative to the retention shaft 32.

The saw blade retention system 10 also includes a pin 90 to cooperate with the cam slots 80. The pin 90 is generally cylindrical in shape and is disposed in a pin aperture 92 extending diametrically through the main portion 40 of the retention shaft 32. Preferably, the pin 90 is made of a softer metal material than the retention shaft 32 or chuck 66 and is press-fit into the pin aperture 92. The pin 90 is of a sufficient length to extend into the cam slots 80. The pin 90 cooperates with the cam slots 80 to limit the rotation of the chuck 66 and allow axial movement of the chuck 66 relative to the retention shaft 32.

Figure 5A:
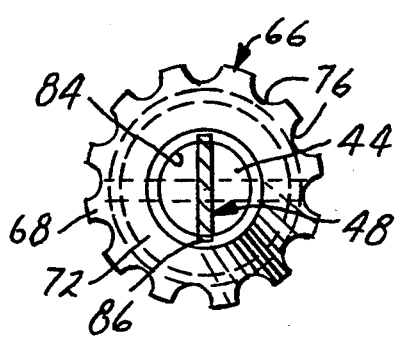
FIG. 5A is a sectional view taken along line 5—5 of FIG. 4 illustrating the saw blade retention system in an unlocked position.
Figure 5B:
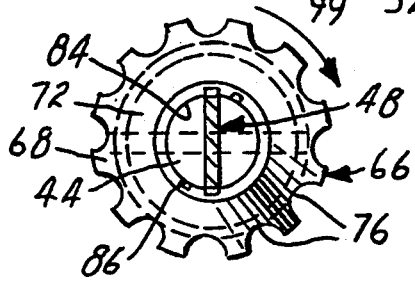
FIG. 5B is a sectional view taken along line 5—5 of FIG. 4 illustrating the saw blade retention system in a locked position.

The saw blade retention system 10 further includes a spring 94 for urging the chuck 66 in a locked position when the pin 90 is at an upper end of the cam slots 80. The spring 94 is a torsional spring having first and second tangs 96 and 98. The spring 94 is disposed in an annular recess 99 extending radially inwardly between the main portion 40 and the first stepped portion 42. The first tang 96 is disposed in a tang pocket 100 extending axially into the body portion 68 of the chuck 66. The second tang 98 is disposed in a tang recess 102 extending axially into the main portion 40 of the retention shaft 32. The spring 94 is wound counterclockwise (e.g., left-hand thread) and, when relaxed, urges the chuck 66 to a locked position as illustrated in FIG. 5B.

In operation, the chuck 66 is rotated relative to the retention shaft 32 by an operator to overcome the force or torque of the spring 94. As the chuck 66 rotates, the cam slots 80 move relative to the pin 90, in turn, moving the chuck 66 axially away from the retention shaft 32. The saw blade retention system 10 has an unlocked position when the slot 86 in the chuck 66 is aligned with the slot 46 in the retention shaft 32 as illustrated in FIG. 5A. In the unlocked position, the pin 90 is at a lower end of the cam slots 80 and interior surface 88 is at a maximum distance from the blade seat 47. The saw blade 48 is inserted through the slot 86 and into the slot 46 until the end edge 56 contacts the blade seat 47.

Next, the chuck 66 is released. The spring 94 relaxes and rotates the chuck 66 relative to the retention shaft 32. As the chuck 66 rotates, the cam slots 80 move relative to the pin 90, in turn, moving the chuck 66 axially toward the retention shaft 32 and reducing the distance between the interior surface 88 and the blade seat 47. Since the chuck 66 and retention shaft 32 are coaxial, the interior surface 88 contacts the inclined edges 64 of the shank portion 54 to provide a force to center the saw blade 48 relative the axial axis A of the retention shaft 32. The saw blade retention system 10 has a locked position when the slot 86 in the chuck 66 are not aligned with the blade-receiving slot 46 in the retention shaft 32 as illustrated in FIG. 5B. In the locked position, the pin 90 is at an upper end of the cam slots 80 and the interior surface 88 and blade seat 47 contact the inclined edges 64 and end edge 56, respectively, of the saw blade 48 to provide a three point pinch or line contact, trapping the saw blade 48 and preventing rotational and axial movement thereof. The operation is reversed to unlock and remove the saw blade 48.

As used herein, the "locked" position refers to the position in which the chuck 66 "locks" or secures the saw blade 48 on the sternal saw 14, and the "unlocked" or "open" position refers to the position in which the chuck 66 does not hold the saw blade in the sternal saw 14. In the "locked" position, the slot 86 of the chuck 66 is not aligned with the blade-receiving slot 46 of the retention shaft 32. In the "unlocked" position, the slot 86 of the chuck 66 is aligned with the blade-receiving slot 46 of the retention shaft 32. As such, the chuck 66 can be "locked" or held in its "unlocked" or "open" position for example by a detent, as discussed below with respect to FIGS. 7-9.

Accordingly, the saw blade retention system 10 incorporates a self-centering blade feature due to the interior surface 88 of the chuck 66 and the inclined edges 64 of the saw blade 48. The saw blade retention system 10 also incorporates a positive axial and radial locking action due to the interior surface 88 and blade seat 47 to trap the saw blade 48. The saw blade retention system 10 also eliminates the use of screws and screwdrivers by providing a ledge 82 and slot 86 for alignment and misalignment with the saw blade 48 and retention shaft 32 to allow insertion and retention of the saw blade 48 to the retention shaft 32.

FIGS. 7 and 8 illustrate an alternative embodiment of the saw blade retention system of the invention, here designated 110. The saw blade retention system 110 includes a blade-retaining chuck 166, similar to chuck 66, but having generally L-shaped cam slots 180. One leg 180A of each of the L-shaped cam slots 180 is similar to cam slots 66, and the other leg 180B of the cam slots 180 provides a detent or locking feature to lock the chuck 166 in its blade-unlocked or open position (FIG. 7) relative to pin 190. Leg 180A will be referred to as the "cam" leg 180A, and leg 180B will be referred to as the "detent" leg 180B.

In its open position (FIG. 7), the chuck 166 will allow saw blades 148 to be inserted into or removed from the chuck 166. The chuck 166 can be moved to its closed or blade-locking position (FIG. 8) by pressing the saw blade 148 or chuck 166 toward the main body of the sternal saw 14 as indicated at F, thereby moving the chuck 166 relative to the pin 190 until the pin 190 is in the cam leg 180A of the chuck 166, and rotating the chuck 166 or allowing the chuck 166 to rotate according to the bias of its torsion spring (not shown but similar in some respects to torsion spring 94) to its closed position. In its closed position, the blade aperture or slot (not shown but similar to slot 86) is not aligned with the blade-receiving slot of the retention shaft (not shown but similar to slot 46 in retention shaft 32) so that the blade 148 cannot be removed from the chuck 166. The longitudinal position that the locked "open" chuck 166 would be in is indicated in phantom in FIG. 8 relative to the "closed" chuck 166.

The torsion spring of the blade retention system 110 is similar in some respects to the torsion spring 94 but in use may be more thoroughly characterized as a compression/torsion spring. The compression/torsion spring provides two different biasing forces having different consequences depending upon whether the pin 190 is in the cam leg 180A or the detent leg 180B.

When the pin 190 is in the cam leg 180A, the compression/torsion spring functions identically to the torsion spring 94 is bias the chuck 166 toward its closed, blade-retaining position, in which the torsional bias of the spring tends to increase the space between the pin 190 and the detent leg 180B of the chuck 166. When the pin 190 is in the detent leg 180B the compressive/expansive bias of the spring urges the chuck 166 away from the retention shaft to releasably lock the pin 190 in the closed end of the detent leg 180B. It will be appreciated that the compression/torsion spring may provide both of these biases, compression and torsion, when the chuck 166 is in its closed and open positions and when moved between those positions but that the practical result of the biases should be to urge the chuck 166 as specified. Alternately, two separate springs (not shown) may be provided, one being a torsion spring similar to torsion spring 94 and the other being a coil compression spring, for example, which merely biases the chuck away from the retention shaft.

In this alternate embodiment, the blade portion 150 of the saw blade 148 is preferably wider than the distance covered between the ends of the blade-receiving slots (not shown but similar to slots 86) so that the longitudinal force F to release the pin 190 from the detent leg 180B may be applied by pushing the saw blade 148 toward the sternal saw. The self-centering feature provided by the inclined edges 64 of the saw blade 48 and the inclined surfaces 88 of the chuck 66 of the embodiment of FIGS. 1-6 may also be provided in the embodiment of FIGS. 7-8.

FIG. 9 illustrates another alternative embodiment of the saw blade retention system, here designated 210, of the invention. Saw blade retention system 210 is similar in many respects to saw blade retention system 110 but additionally includes a detent notch 281 for releasably holding the chuck 266 relative to the pin 290 in the open position, and the cam slot 280 additionally includes an open end 280C allowing the chuck 266 to be placed on the sternal saw while the pin 290 is in the retention shaft.

The saw blade retention system 210 may be assembled after the pin 290 has been inserted into the retention shaft (not shown but similar to retention shaft 32) by aligning the open ends 280C of the cam slots 280 relative to the free ends of the pin 290 and pushing the chuck 266 onto the retention shaft. When the pin 290 has reached the inner end of the open portion 280C of the cam slot 280, the chuck 266 is rotated to bring the pin 290 into the cam leg 280A of the cam slot 280. The cam leg 280A includes the detent notch 281 for releasably locking the chuck 266 in its locked, blade-retaining position on the pin 290.

The open portion 280C of the cam slot 280 and the other portions 280A and 280B of the cam slot 280 define a cantilever arm 267 that, while stiff, has some springiness or flexibility so as to deflect slightly when the pin 290 is moved in or out of the detent notch 281. The cantilever arm 267, however, is preferably sufficiently stiff that the pin 290 cannot pass over a raised stop 267A at its free end when a blade (not shown but similar to blade 48 or 148) is inserted in the chuck 266. The chuck 266, however, can be released from the pin 290 for cleaning or maintenance when a blade (not shown) is not inserted into the chuck 266 by simply turning the chuck 266 relative to the pin 290 until the pin 290 is received in the open portion 280C of the cam slot 280.

As various changes could be made in the above constructions without departing from the scope of the invention, it is intended that all matter contained in the above description or shown in the drawing be interpreted as illustrative and not in a limiting sense.

I claim:

1. A saw blade retention system for retaining a saw blade to a reciprocating saw, the saw blade being elongate and having a longitudinal axis, opposite side edges, a generally planar end edge generally perpendicular to the longitudinal axis of the saw blade, and two generally inclined edges adjacent opposite side edges of the blade and sloped in the direction away from the planar end edge, the saw blade retention system comprising:

a shaft connected to a saw for reciprocation along an axis of reciprocation, and having receiving means for receiving a saw blade, the receiving means having a generally flat surface generally perpendicular to the axis of reciprocation for abutting the generally planar end edge of the saw blade;

a chuck disposed about the shaft and having alignment means aligned with the receiving means in an unlocked position for allowing the saw blade to be disposed in the receiving means; and rotation means for allowing the chuck to rotate angularly relative to the saw blade and the shaft to a locked position to prevent the saw blade from exiting the receiving means and for allowing the chuck to move axially relative to the shaft to prevent axial movement of the saw blade between the chuck and the shaft;

the chuck having a generally frustoconical, annular, internal ledge at an inclined angle relative to the generally flat surface of the receiving means, the ledge and the generally flat surface of the saw blade retention system constituting centering means for centering a saw blade inserted in the saw blade retention system by interacting with the planar end edge and inclined edges of the saw blade to bring the saw blade into longitudinal alignment with the axis of reciprocation.

2. A saw blade retention system as set forth in claim 1 wherein the rotation means comprises at least one cam slot formed on either one of the chuck and shaft and at least one pin extending from the other one of the chuck and shaft and into the cam slot, the cam slot extending helically relative to the axis of rotation of the chuck.

3. A saw blade retention system as set forth in claim 1 wherein the alignment means comprises a first slot extending through the frustoconical ledge, the receiving means being formed as a second slot at one end of the shaft, the second slot having a closed end defining the generally flat surface of the receiving means.

4. A saw blade retention system as set forth in claim 3 including urging means for urging the chuck to the locked position, the urging means comprising a torsional spring interconnected between the chuck and the shaft.

5. A saw blade retention system for a reciprocating saw comprising:

a generally elongate saw blade having a longitudinal axis, opposite side edges, a generally planar end edge generally perpendicular to the longitudinal axis of the saw blade, and two generally inclined edges adjacent opposite side edges of the blade and sloped in the direction away from the planar end edge;

a shaft connected to a saw for reciprocation along an axis of reciprocation and having receiving means for receiving the saw blade;

a chuck disposed about the shaft and having alignment means aligned with the receiving means in an unlocked position for allowing the saw blade to be disposed in the receiving means; and rotation means for allowing the chuck to rotate angularly relative to the saw blade and the shaft to a locked position to prevent the saw blade from exiting the receiving means and for allowing the chuck to move axially relative to the shaft to prevent axial movement of the saw blade between the chuck and the shaft.

6. A saw blade retention system as set forth in claim 5 wherein the rotation means comprises at least one cam slot formed on either one of the chuck and shaft and at least one pin extending from the other one of the chuck and shaft and into the cam slot, the cam slot extending helically relative to the axis of rotation of the chuck.

7. A saw blade retention system as set forth in claim 5 wherein the saw blade comprises a blade portion having a plurality of teeth, a shank portion extending from the blade portion for connection to a reciprocating saw, and means forming a pair of recesses opposing each other from edges of the shank portion.

8. A saw blade retention system as set forth in claim 5 including centering means for centering the longitudinal axis of the saw blade with respect to the axis of reciprocation of the shaft, the centering means comprising opposed inclined surfaces on the chuck oriented and positioned in the chuck to engage the inclined edges of the saw blade to center the saw blade relative to the axis of reciprocation of the shaft.

9. A saw blade retention system as set forth in claim 8 wherein the chuck has an outer end, the inclined surfaces of the chuck comprising an inclined surface of an internal annular ledge in the chuck generally adjacent the outer end of the chuck, the alignment means comprising a first slot extending through the internal ledge, the receiving means being formed as a second slot at one end of the shaft, the second slot having a generally flat surface generally perpendicular to the axis of reciprocation of the shaft.

10. A saw blade retention system as set forth in claim 9 including urging means for urging the chuck toward the locked position, the urging means comprising a torsional spring interconnected between the chuck and the shaft.

11. A saw blade retention system for a reciprocating saw comprising:
a saw blade comprising a blade portion having a plurality of teeth, a shank portion extending from the blade portion for connection to a reciprocating saw, and means forming a pair of recesses opposing each other from edges of the shank portion; the shank portion having a planar end edge, planar side edges generally perpendicular to the end edge, and planar inclined edges extending from the side edges into the recesses and away from the end edge;
a shaft connected to a saw for reciprocation and having receiving means for receiving the saw blade;
a chuck disposed about the shaft and having alignment means aligned with the receiving means in an unlocked position for allowing the saw blade to be disposed in the receiving means; and
rotation means for allowing the chuck to rotate angularly relative to the saw blade and the shaft to a locked position to prevent the saw blade from exiting the receiving means and for allowing the chuck to move axially relative to the shaft to prevent axial movement of the saw blade between the chuck and the shaft.

12. A saw blade retention system for a reciprocating saw comprising:
a saw blade, the saw blade comprising a blade portion having a plurality of teeth, a shank portion extending from the blade portion, and means forming a pair of recesses opposing each other from edges of the shank portion, the shank portion having a planar end edge, planar side edges generally perpendicular to the end edge, and planar inclined edges extending from the side edges into the recesses and away from the end edge;
a shaft connected to a saw for reciprocation and having means forming a first slot at one end of the shaft for receiving the shank portion of the saw blade;
a chuck disposed about the shaft and having a ledge extending radially inwardly at one end and forming a second slot extending therethrough aligned with the first slot in an unlocked position for allowing the saw blade to be disposed in the first slot;
means forming cam slots on either one of the chuck and shaft and a pin extending from the other one of the chuck and shaft and into the cam slots for allowing the chuck to rotate angularly relative to the saw blade and the shaft to a locked position, in which the first and second slots are not aligned, and for allowing the chuck to move axially relative to the shaft to prevent axial movement of the saw blade between the chuck and the shaft; and
opposed inclined surfaces on the chuck that cooperate with the inclined edges of the saw blade to center an axial/longitudinal axis of the saw blade with an axial axis of the shaft.

13. A saw blade retention system as set forth in claim 12 wherein the cam slots extend helically relative to the axis of rotation of the chuck.

14. A saw blade retention system as set forth in claim 12 including urging means for urging the chuck in the locked position, the urging means comprising a torsional spring interconnected between the chuck and the shaft.

15. A saw blade retention system as set forth in claim 12 wherein the inclined edges of the saw blade are at an angle of about twenty degrees relative the end edge.

16. A saw blade retention system as set forth in claim 12 wherein the end edge of the saw blade is generally perpendicular to a longitudinal axis of the saw blade.

17. A saw blade retention system for a reciprocating saw, the system comprising:
a surgical saw blade comprising a blade portion having a plurality of teeth; a shank portion extending from the blade portion for connection to a reciprocating saw, the blade having a longitudinal axis extending through the blade and shank portions, the shank portion being generally planar having opposite major surfaces, opposite lateral edges and an end edge, the shank portion including recess-defining edges defining a pair of recesses opposing each other extending generally laterally inwardly along the shank portion from the opposite edges of the shank portion, and the recess-defining edges including at least one inclined edge with respect to each recess extending at an inclined angle relative to the end edge;
a shaft connected to a saw for reciprocation and having a first blade-receiving slot at one end of the shaft for receiving the shank portion of the saw blade, the blade-receiving slot having a bottom end and an open end;
a chuck disposed about the shaft and having a annular ledge extending radially inwardly at one end to define a blade-receiving opening having a diameter at least as large as the distance between the opposing recesses of the saw blade but less than the distance between the lateral edges of the shank portion of the saw blade, the ledge having a second blade-receiving slot extending therethrough and generally radially outwardly from the opening, the chuck being mounted on the saw for rotation relative to the shaft between an unlocked position, wherein the second blade-receiving slot is aligned with the first blade-receiving slot to allow the saw blade to be inserted into the first and second blade-receiving slots, and a locked position, wherein the first and second blade-receiving slots are not aligned such that the ledge of the chuck holds the saw blade in the first blade-receiving slot;

the ledge of the chuck having a generally frustoconical surface generally complementary to the inclined edges of the saw blade for engagement with the inclined edges of the saw blade when the chuck is moved to its locked position such that the end edge of the saw blade is held against the bottom of the first blade-receiving slot and the saw blade tends to be centered by the forces applied by the frustoconical surface and the bottom of the first blade-receiving slot.

18. A blade retention system according to claim 17 further comprising cam slots in one of the chuck and shaft, and a pin mounted on the other of the chuck and shaft and extending into the cam slots, the cam slots being disposed at a helical angle relative to the axis of rotation of the chuck such that the frustoconical surface of the ledge moves closer to the bottom of the first blade-receiving slot as the chuck is rotated from its unlocked position toward its locked position.

19. A blade retention system according to claim 18 wherein the inclined edges of the saw blade are disposed at an angle of approximately 20 degrees relative to the end edge of the saw blade, the frustoconical surface of the chuck being disposed at an angle of approximately 20 degrees relative to the bottom of the first blade-receiving slot, and the helical angle of the cam slots being approximately eight degrees.

20. A blade retention system according to claim 18 further comprising biasing means for biasing the chuck toward its locked position.

21. A blade retention system according to claim 20 wherein the biasing means comprises a torsion spring operatively linked with the chuck and shaft to bias the chuck toward its locked position relative to the shaft.

22. A blade retention system according to claim 21 further comprising detent means for releasably securing the chuck in its unlocked position to facilitate inserting a saw blade.

* * * * *